United States Patent [19]

Coppola et al.

[11] Patent Number: 5,599,917
[45] Date of Patent: Feb. 4, 1997

[54] INHIBITION OF INTERFERON-γ WITH OLIGONUCLEOTIDES

[75] Inventors: George R. Coppola, Hartsdale; Bruce A. Beutel, Suffern, both of N.Y.; Arthur H. Bertelsen, Ridgewood, N.J.

[73] Assignee: PharmaGenics, Inc., Allendale, N.J.

[21] Appl. No.: 210,222

[22] Filed: Mar. 17, 1994

[51] Int. Cl.⁶ .............. C12N 15/00; C12N 5/00; A61K 48/00
[52] U.S. Cl. .......... 536/22.1; 536/23.1; 536/24.1; 536/24.2; 536/24.5
[58] Field of Search .......... 530/351; 536/23.52, 536/23.1, 22.1, 24.1, 24.2; 435/69.57, 6, 91.1; 514/44, 2

[56] References Cited

U.S. PATENT DOCUMENTS

| | | | |
|---|---|---|---|
| 5,087,617 | 2/1992 | Smith | 514/44 |
| 5,190,873 | 3/1993 | Lernhardt et al. | 435/177 |
| 5,212,083 | 5/1993 | Haldenwang | 435/207 |
| 5,248,671 | 9/1993 | Smith | 514/44 |
| 5,270,163 | 12/1993 | Gold et al. | 435/6 |
| 5,459,015 | 10/1995 | Janjic et al. | 435/6 |

FOREIGN PATENT DOCUMENTS

WO92/14843  9/1992  WIPO.

OTHER PUBLICATIONS

Jacob et al., *J. Exp. Med.*, 166:798(1987).
Umland et al., *Clin. Immun. Immunopath.*, 63:66(1992).
Bock et al., *Nature*, 355:565 (1992).
Aguet et al. *Cell* 55:273–280 (1988).
Balkwill et al *Immunol Today* 10(9):299–303 (1989).
Gimble et al *Exp Hemat.* 21:224–230 (1993).
Guha et al *Cell. Immunol* 151(2):404–413.
Valente et al *Eur. J Immunol* 22:2403–2412 (1992).

*Primary Examiner*—Jacqueline M. Stone
*Assistant Examiner*—Andrew Milne
*Attorney, Agent, or Firm*—Charles J. Herron; Elliot M. Olstein

[57] ABSTRACT

Oligonucleotides and analogs thereof that bind to and preferably modulate the activity of interferon-γ, and methods for their use, including therapeutic and diagnostic methods are disclosed.

2 Claims, 3 Drawing Sheets

INHIBITION OF INTERFERON-γ WITH OLIGONUCLEOTIDES

Interferon-γ (IFN-γ) is a multifunctional cytokine produced by, and secreted from, both T-lymphocytes and NK cells. The multiple forms of the cytokine all have an N-terminal pyroglutamic acid residue and up to two N-linked carbohydrates. The largest mature form of the cytokine consists of 143 amino acids but the carboxyl end of the protein is apparently heterogeneous due to post-translational proteolysis (Rinderkneckt et al., 1984, J. Biol. Chem. Vol. 259 p.6790).

IFN-γ exhibits antiviral activity as well as numerous immunomodulatory and anti-proliferative effects. Its effects on the immune system include influencing B-cell immunoglobulin class switching (Snapper et al., 1992, J. Exp. Med., 175:1367), up-regulating class I and class II MHC antigen expression (Buckmeier and Schreiber, 1985, Proc. Natl. Acad. Sci. USA, 82:404; Bancroft et al., 1992, Immunol., 143:127), stimulating conversion of Th1 to Th2 lymphocytes (Kanagawa et al., 1993, Science, 262:240), increasing macrophage-mediated killing of intracellular parasites (Portnoy, 1992, Curr. Opin. Immunol., 4:20) and promoting the production of IL-1, tumor necrosis factor, platelet activating factor, phosphoinositol kinase, 2-5A synthetase, indoleamine, 2,3 dioxygenase, hydrogen peroxide, pterin and nitric oxide (Nathan and Hibbs, 1991, Curr. Opin. Immunol., 3:95; Grossberg et al., 1989, Experientia, 45:508; Adolf, 1985, Oncology (suppl. 1), 4:33; Samuel, 1991, Virology, 183:1; Billiau and Dijkmans, 1990, Biochem. Pharmacol. 40:1433; Harris, et al., 1992, J. Biol. Chem. 265:17868; Staeheli, et al., 1990, Adv. Virus Res. 38:147). These various activities of IFN-γ are mediated by its binding to a specific cell-surface receptor protein found on a range of different cell types (Aguet et al., 1988, Cell, 55:273; Valente et al., 1992, Eur. J. Immunol., 22:2403).

Whereas many of the effects of IFN-γ on the immune system are beneficial to health and well-being, the activity of IFN-γ has also been shown to exacerbate certain pathological conditions. Immune system over-stimulation by IFN-γ has been implicated as a mediator of autoimmune reactions, as a contributing factor in the damage caused by septic shock and as contributing to the decline of immunocompetence in HIV infected individuals. Neutralizing antibodies directed against IFN-γ have been investigated as therapeutics in a number of disease model systems (Jacob et al., 1987, J. Exp. Med., 166:798; Umland et al. 1992, Clin. Immun. Immunopath., 63:66).

In a principal aspect this invention provides compounds that can bind to, and block the activity of, IFN-γ. In particular it has been discovered that certain oligonucleotides bind tightly to IFN-γ and block interaction with its specific receptor protein thereby neutralizing cytokine activity. The inhibitory oligonucleotides contain discrete sequences that impart specific interaction with IFN-γ. Since the oligonucleotides of the instant invention bind tightly and specifically with IFN-γ it is a further object of the invention to provide diagnostic reagents and methods for detecting the presence of IFN-γ in test samples.

FIG. 1

The binding of $^{32}$P-labelled oligonucleotides (at tracer concentrations) to various concentrations of IFN-γ.

FIG. 2

Elisa assay of IFN-γ receptor binding to plate-bound IFN-γ determining the inhibition of the interaction by added oligonucleotides.

FIG. 3

Elisa assay of IFN-γ interaction with plate-bound IFN-γ receptor determining the inhibition of the interaction amounts of added oligonucleotides.

The present invention identifies oligonucleotides for binding with and preferably thereby modulating, inhibiting or enhancing, the activity or function of interferon-γ. The oligonucleotides are those which are capable of binding with reasonable affinity, preferably at a site which modulates the activity of the target molecule, IFN-γ. Such IFN-γ binding oligonucleotides can also be useful as diagnostic reagents for measuring levels of the cytokine.

Oligonucleotide compounds have been discovered that bind IFN-γ with high affinity and selectivity. Therefore, a principal aspect of the invention provides numerous oligonucleotides and portions of them that modulate, e.g. inhibit, the activity of IFN-γ upon binding therewith. Oligonucleotides or poynucleotides are hereafter sometimes collectively referred to as "nucleic acid(s)". The nucleic acids so identified are not previously known to modulate IFN-γ activity and are preferably modified or unmodified nucleic acids containing one or more discrete, short (i.e. not more that about 20 bases) sequence elements. The nucleic acid can include flanking sequence at at least one of the 3' and 5' end(s).

More particularly, the preferred oligonucleotides of the invention are those that bind with IFN-γ at a Kd of not more than about 30 nM. Kd is determined by the method described in Riggs, et al., 1970, J. Mol. Biol., 48:67–83.

In another aspect the invention provides nucleic acids or analogs thereof that bind to and affect the activity of IFN-γ and are preferably selected from the group consisting of SEQ ID NOS:1 to 29 including most particularly those oligonucleotides containing one or more sequences selected from the group consisting of SEQ ID NOS: 30 to 34.

Oligonucleotides of the present invention were effective in inhibiting IFN-γ activity when they included at least one of the following sequences: AAGUUG (SEQ ID NO:30); UGANGCUC (SEQ ID NO:31); UAAGUUGANGCUCG (SEQ ID NO:32); GCACCNC (SEQ ID NO:33); GCCACCUCG (SEQ ID NO:34). Nucleic acid sequences are referred to using standard IUPAC abbreviation to specify the identity of the bases at individual positions of the oligomer.

A variety of fragments of individual oligonucleotides have been shown to bind tightly to IFN-γ. For example, various subsequences of SEQ ID NO:3, identified in the SEQUENCE LISTING as SEQ ID NO:35 through SEQ ID NO:39, show a similar degree of binding to IFN-γ as the full length (98-base) oligonucleotide.

In addition to oligonucleotides having SEQ ID Nos. 1 through 39, the present invention further contemplates other oligonucleotides that bind to IFN-γ, and preferably inhibit the function thereof. Such additional oligonucleotides can be obtained readily by one of ordinary skill in the art using a variety of methods including, but not limited to, those described in Kinzler and Vogelstein, 1989, *Nucleic Acids Research*, Vol. 17, pgs. 3645–3652; Oliphant, Brandl and Struhl, 1989, *Molecular and Cellular Biology*, Vol. 9, pgs. 2944–2949; Kinzler and Vogelstein, *Molecular and Cellular Biology*, Vol. 10, pgs. 634–642; Thiesen and Bach, 1990, *Nucleic Acids Research*, Vol. 18, pgs. 3203–3209; Tuerk and Gold, 1990, *Science*, Vol. 249, pgs. 505–510; Ellington and Szostak, 1990, *Nature*, Vol. 346, pgs. 818–822; Gold and Tuerk, U.S. Pat. No. 5,270,163 and Beutel et al., U.S. Patent application Ser. No. 08/079,677.

The oligonucleotides of the invention may be in the form of a single strand, a double strand, a stem-loop, a bulged helix, a pseudoknot or a closed-circular structure.

In another aspect the invention provides a method of inhibiting IFN-γ function. The method comprises contacting IFN-γ with an effective amount of an oligonucleotide, or a molecule containing such an oligonucleotide, which inhibits IFN-γ function.

The term "inhibiting IFN-γ function" as used herein, means that the oligonucleotide prevents IFN-γ from being active, preferably by binding to IFN-γ. IFN-γ is a multifunctional cytokine produced by both T lymphocytes and NK cells. The effects of IFN-γ are mediated through binding to a specific transmembrane receptor, with the resultant activation and intracellular translocation of at least two known DNA-binding proteins.

In their several aspects, the methods of use of the nucleic acid sequences of the invention include inhibition of IFN-γ's antiviral activity, as well as its pleiotropic immunomodulatory and cell growth inhibitory effects.

Among the immunoregulatory effects of IFN-γ which can be modulated or inhibited are its influence on the class of antibody produced by B cells, its up-regulation of both class I and II MHC antigens, and its effect in increasing macrophage-mediated killing of intracellular parasites. All of these functions can be modulated or inhibited by the method of contacting IFN-γ with the nucleic acid sequences of the invention.

Another use in accordance with the invention is to inhibit the effect of IFN-γ to induce several genes, including HLA-B and HLA-DR, IP-10, P1 kinase, 2,5A-synthetase, and indoleamine 2,3-dioxygenase.

Another aspect of the invention provides the ability to inhibit the effect of IFN-γ to promote the production of interleukin-1 (IL-1), tumor necrosis factor (TNF), platelet activating factor, $H_2O_2$, and pterin.

Very interestingly, the invention provides a method to inhibit the propensity for IFN-γ to induce its own expression.

Yet another advantageous use provided by the inhibitory method of the invention is where an IFN-γ-inhibitory nucleic acid limits inappropriate IFN-γ-stimulated inflammatory responses in septic shock or rheumatoid arthritis.

Quinolinic acid, produced by the metabolic pathway catalyzed by 2,3-dioxygenase, damages neurons. Another of the many uses of the inhibitory method of the invention is the suppression of induction of this enzyme by an IFN-γ-inhibitory nucleic acid.

HIV-infected patients are less likely to develop AIDS if their CD4+ cells remain as Th1 as opposed to Th2. Since IFN-γ is implicated in the induction of a Th1 conversion to Th2 class, the IFN-γ-inhibitory nucleic acids of the invention are beneficial to HIV-infected individuals.

With respect to all of these aspects the term "inhibiting" refers to inhibiting one or more of the foregoing functions.

Nucleic acids that interact with proteins with high affinity are comprised of individual sequence elements that are highly conserved and other elements in which sequence is less well-conserved or even non-conserved. Both kinds of elements are important for the interaction of the nucleic acid and protein. For example, the sequence-specific elements might be the region that makes specific contacts with the protein whereas the less conserved regions might serve a structural role in the presentation of the specific elements in the preferred configuration for protein binding. Furthermore, oligonucleotide polymers may be modified at many positions to impart new properties, such as resistance to nucleases, without destroying the desired characteristics of the oligonucleotide including its interaction with a target. For example, a ribozyme oligonucleotide generally consists of ribonucleotides yet many positions of the ribozyme oligonucleotide may be substituted with deoxyribonucleotides, making it more resistant to ribonucleases, without affecting its catalytic activity on its target RNA. Thus, the oligonucleotides of the present invention may be modified in a variety of ways to change certain characteristics, such as resistance to nucleases or ease of manufacture.

The term "oligonucleotide" as used herein means that the oligonucleotide may be a ribonucleic acid, i.e. an RNA oligonucleotide; a deoxyribonucleic acid, i.e. a DNA oligonucleotide; or a mixed ribonucleic/deoxyribonucleic acid; i.e., the oligonucleotide may include ribose or deoxyribose sugars, 2'-O-methyl ribose or other 2' substituted or conjugated sugars, or a mixture of such sugars. Alternatively, the oligonucleotide may include other 5-carbon or 6-carbon sugars, such as, for example, arabinose, xylose, glucose, galactose, or deoxy derivatives thereof or any mixture of sugars.

One or more of the phosphorus-containing moieties of the oligonucleotides of the present invention may be modified or unmodified. The phosphorus-containing moiety may be, for example, a phosphate, phosphonate, alkylphosphonate, aminoalkyl phosphonate, alkyl-thiophosphonate, phosphoramidate, phosphorodiamidate, phosphorothioate, phosphorodithioate, phosphorothionate, phosphorothiolate, phosphoramidothiolate or phosphorimidate. It is to be understood, however, that the scope of the present invention is not to be limited to any specific phosphorus moiety or moieties. Also, one or more phosphorus moieties may be modified with a cationic, anionic, or zwitterionic moiety. The oligonucleotides may also contain one or more backbone linkages which do not contain phosphorus, such as carbonates, carboxymethyl esters, acetamidates, carbamates, acetals, and the like. The oligonucleotides may also contain one or more backbone linkage of peptide nucleic acids. (Egholm, et al., *J. Am. Chem. Soc.,* 114:1895–1897 (1992)).

The oligonucleotides of the invention also include any natural or unnatural, substituted or unsubstituted, purine or pyrimidine base. Such purine and pyrimidine bases include, but are not limited to, natural purines and pyrimidines such as adenine, cytosine, thymine, guanine, uracil, or other purines and pyrimidines, or analogs thereof, such as isocytosine, 6-methyluracil, 4,6-di-hydroxypyrimidine, hypoxanthine, xanthine, 2,6-diaminopurine, 5-azacytosine, 5-methyl cystosine, 7-deaza-adenine, 7-deaza-guanine, and the like.

The oligonucleotides of the invention may be modified such that at least one nucleotide unit of the oligonucleotides may include a conjugate group. Such conjugate groups include, but are not limited to, (a) amino acids, including D-amino acids and L-amino acids; (b) peptides, polypeptides, and proteins; (c) dipeptide mimics; (d) sugars; (e) sugar phosphates; (f) neurotransmitters; (g) hormones; (h) poly (hydroxypropylmethacrylamide); (i) polyethylene imine; (j) dextrans; (k) polymaleic anhydride; (l) cyclodextrins; (m) starches; (n) steroids, including sterols such as, but not limited to, cholesterol; (o) acridine; (p) vitamins; and (q) polyalkylene glycols, such as polyethylene glycol. Such moieties may make the oligonucleotides more resistant to degradation in cells and in the circulation, and/or make the oligonucleotides more permeable to cells. The conjugate moiety may be attached to the 3' terminal nucleotide unit and/or the 5' terminal nucleotide unit and/or to an internal nucleotide unit(s), or conjugate moieties may be attached to two or more nucleotide units at the 3' end and/or the 5' end of the oligonucleotide. In one embodiment, substituted nucleotide units may alternate with unsubstituted nucleotide units. In another embodiment, all of the nucleotide units are substituted with a conjugate moiety.

The conjugate moiety may be attached to the oligonucleotide at the purine or pyrimidine base, at the phosphate group, or to the sugar. When the conjugate moiety is attached to the base, it is preferably attached at certain positions of the base, depending upon the base to which the moiety is attached. When the moiety is attached to adenine, it may be attached at the C2, N6, or C8 positions. When the moiety is attached to guanine, it may be attached at the N2 or C8 positions. When the moiety is attached to cytosine, it may be attached at the C5 or N4 positions. When the moiety is attached to thymine or uracil, it may be attached at the C5 position.

In one embodiment, the oligonucleotide includes from about 5 to about 100 nucleotide units, preferably from about 8 to about 60 nucleotide units.

In yet another embodiment, the oligonucleotide represents a portion of a larger molecule which contains non-oligonucleotide components, such as, for example, peptides or proteins, or simple carbohydrates, and lipids.

The oligonucleotides of the present invention may be in the form of a single strand, a double strand, a stem-loop structure, a pseudoknot, or a closed, circular structure. In one embodiment, the ends of the oligonucleotide may be bridged by non-nucleotide moieties. Examples of non-nucleotide bridging moieties include, but are not limited to, those having the following structural formula:

$T_1$—R—$T_2$, where $T_1$ and $T_2$ are each independently attached to a nucleotide phosphate moiety or a hydroxyl moiety. R is selected from the group consisting of (a) saturated and unsaturated hydrocarbons; (b) polyalkylene glycols; (c) polypeptides; (d) thiohydrocarbons; (e) polyalkylamines; (f) polyalkylene thioglycols; (g) polyamides; (h) disubstituted monocyclic or polycyclic aromatic hydrocarbons; (i) intercalating agents; (j) monosaccharides; and (k) oligosaccharides; or mixtures thereof. In one embodiment, the non-nucleotide bridging moiety may be a polyalkylene glycol such as polyethylene glycol.

In another embodiment, one or more of the non-nucleotide moieties R may be substituted for one or more of the nucleotide units in the target protein binding sequences, as hereinabove mentioned.

The oligonucleotides of the present invention may be synthesized by a variety of accepted means known to those skilled in the art. For example, the oligonucleotides may be synthesized on an automated nucleic acid synthesizer. Alternatively, the oligonucleotides may be synthesized enzymatically through the use of flanking or primer sequences at the 5' and 3' ends. In another alternative, the oligonucleotides may be synthesized by solution phase chemistry. It is to be understood, however, that the scope of the present invention is not to be limited to any particular means of synthesis.

The oligonucleotides of the present invention may be administered in conjunction with an acceptable pharmaceutical carrier as a pharmaceutical composition. Such pharmaceutical compositions may contain suitable excipients and auxiliaries which facilitate processing of the active compounds into preparations which can be used pharmaceutically. Such oligonucleotides may be administered by intramuscular, intraperitoneal, intraveneous, or subdermal injection in a suitable solution. Preferably, the preparations, particularly those which can be administered orally and which can be used for the preferred type of administration, such as tablets, dragees and capsules, and preparations which can be administered rectally, such as suppositories, as well as suitable solutions for administration parenterally or orally, and compositions which can be administered buccally or sublingually, including inclusion compounds, contain from about 0.1 to 99 percent by weight of active ingredients, together with the excipient. It is also contemplated that the oligonucleotides may be administered topically.

The pharmaceutical preparations of the present invention are manufactured in a manner which is itself well known in the art. For example, the pharmaceutical preparations may be made by means of conventional mixing, granulating, dragee-making, dissolving or lyophilizing processes. The process to be used will depend ultimately on the physical properties of the active ingredient used.

Suitable excipients are, in particular, fillers such as sugar, for example, lactose or sucrose, mannitol or sorbitol, cellulose preparations and/or calcium phosphates, for example, tricalcium phosphate or calcium hydrogen phosphate, as well as binders such as starch or paste, using, for example, maize starch, wheat starch, rice starch, potato starch, gelatin, gum tragacanth, methyl cellulose, hydroxypropylmethylcellulose, sodium carboxypropylmethylcellulose, sodium carboxymethylcellulose, and/or polyvinyl pyrrolidone. If desired, disintegrating agents may be added, such as the above-mentioned starches as well as carboxymethyl-starch, cross-linked polyvinyl pyrrolidone, agar, or alginic acid or a salt thereof, such as sodium alginate. Auxiliaries are flow-regulating agents and lubricants, such as, for example, silica, talc, stearic acid or salts thereof, such as magnesium stearate or calcium stearate, and/or polyethylene glycol. Dragee cores may be provided with suitable coatings which, if desired, may be resistant to gastric juices. For this purpose, concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dyestuffs and pigments may be added to the tablets of dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the oligonucleotide in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble or water-dispersible form. In addition, suspensions of the active compounds as appropriate oil injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension including, for example, sodium carboxymethyl cellulose, sorbitol and/or dextran. Optionally, the suspension may also contain stabilizers.

Additionally, the compounds of the present invention may also be administered encapsulated in liposomes, wherein the active ingredient is contained either dispersed or variously present in corpuscles consisting of aqueous concentric layers adherent to lipidic layers. The active ingredient, depending upon its solubility, may be present both in the aqueous layer, in the lipidic layer, or in what is generally termed a liposomic suspension. The hydrophobic layer, generally but not exclusively, comprises phospholipids such as lecithin and sphingomycelin, steroids such as cholesterol, surfactants such as dicetylphosphate, stearylamine, or phosphatidic acid, and/or other materials of a hydrophobic nature. The diameters of the liposomes generally range from about 15 nm to about 5 microns.

The oligonucleotides are administered to a host, such as a human, in an amount effective to inhibit the IFN-γ function. Thus, the oligonucleotides may be used prophylactically or therapeutically. Preferably, the oligonucleotides are administered to a host so as to provide a concentration of oligonucleotide in the blood of from about 10 nanomolar to about 500 micromolar, preferably from about 5 micromolar to about 100 micromolar. It is also contemplated that the oligonucleotides may be administered in vitro or ex vivo as well as in vivo.

The oligonucleotides of the present invention may also be employed as diagnostic probes for determining the presence of IFN-γ, and thereby determining the need for modulation of its function or activity. In such embodiments, a modified or unmodified oligonucleotide of the present invention is added to a sample suspected of containing IFN-γ. The oligonucleotide may be labeled with a detectable marker, including but not limited to, a radioisotope, a biotin moiety, a chromophore, a fluorescent moiety, or an enzyme label. Thus, the oligonucleotide may be employed in a variety of assay methods for the detection of IFN-γ, such methods including sandwich assays, competitive assays, ELISA, inhibition assays, and other assays known to those skilled in the art.

It is to be understood, however, that the scope of the present invention is not to be limited to the specific embodiments described above. The invention may be practiced other than as particularly described and still be within the scope of the accompanying claims.

The following examples illustrate oligonucleotide binding to IFN-γ and inhibition of IFN-γ binding with its receptor protein.

EXAMPLE 1

Oligonucleotide Binding to IFN-γ

Figure 1:
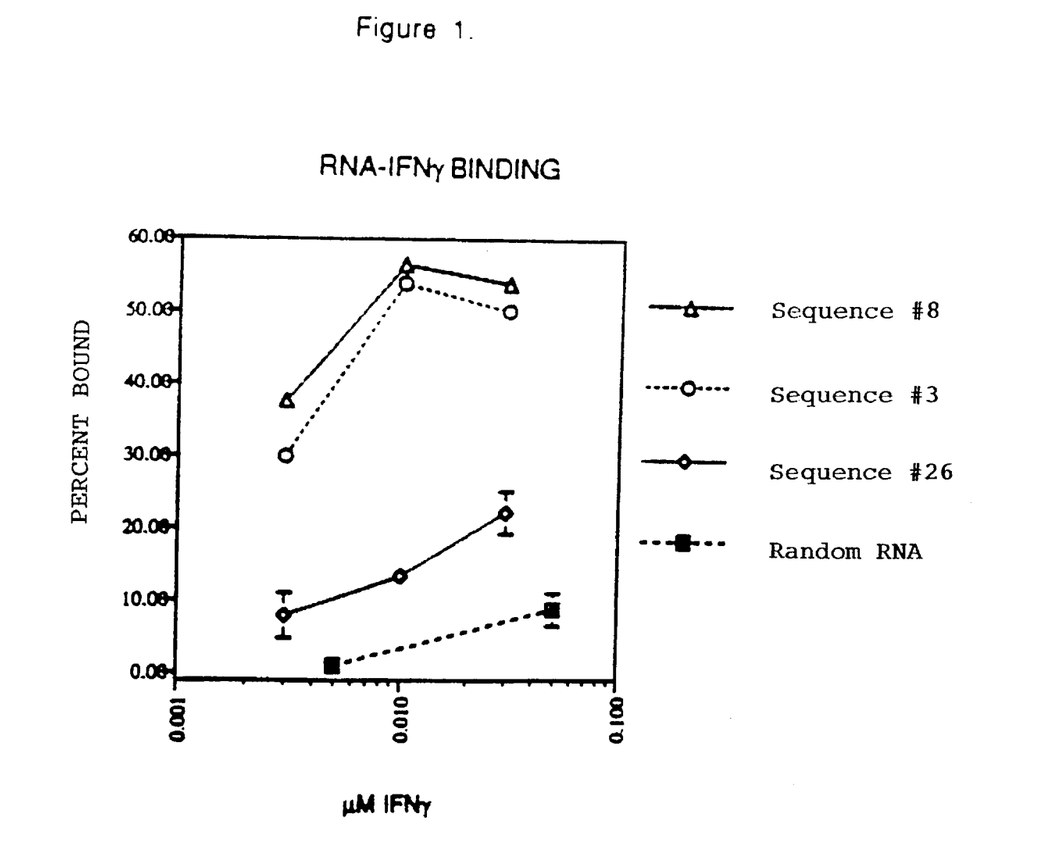

In order to demonstrate that oligonucleotides were capable of binding tightly to IFN-γ they were synthesized on an oligonucleotide synthesizer to have a specified sequence. In the case of RNA oligonucleotides, the oligonucleotide either was synthesized directly as RNA or else the corresponding DNA sequence was synthesized and the RNA to be tested was generated by in vitro transcription of the DNA using a mixture of nucleoside triphosphates and T7 RNA polymerase. The synthetic oligonucleotides were $^{32}$P-labelled either at the 5' end using $\gamma^{32}$P-ATP and T4 polynucleotide kinase or internally using ($\alpha^{32}$P-NTPS in the transcription reaction. Portions of the labelled oligonucleotide being tested were incubated with various concentrations of IFN-γ in a binding buffer of 25 mM Tris-HCl pH 7.5, 150 mM NaCl, 3mM $MgCl_2$ for about 20 minutes at ambient temperature (ca. 23° C.). The labelled oligonucleotide bound to IFN-γ protein was recovered by filtration of the binding reaction through a nitrocellulose filter. After washing the filter with excess binding buffer, the radioactive oligonucleotide retained by the filter was determined by scintillation counting and the percentage of the counts retained was plotted against the concentration of protein present in the binding reaction. FIG. 1 presents representative results for oligonucleotides of the invention (SEQ ID NOS: 3, 8 AND 26). Also shown in FIG. 1 is the much weaker binding of a mixture of 98 base random-sequence RNA to IFN-γ.

EXAMPLE 2

Oligonucleotides inhibit binding of IFN-γ with IFN-γ receptor

Figure 2:
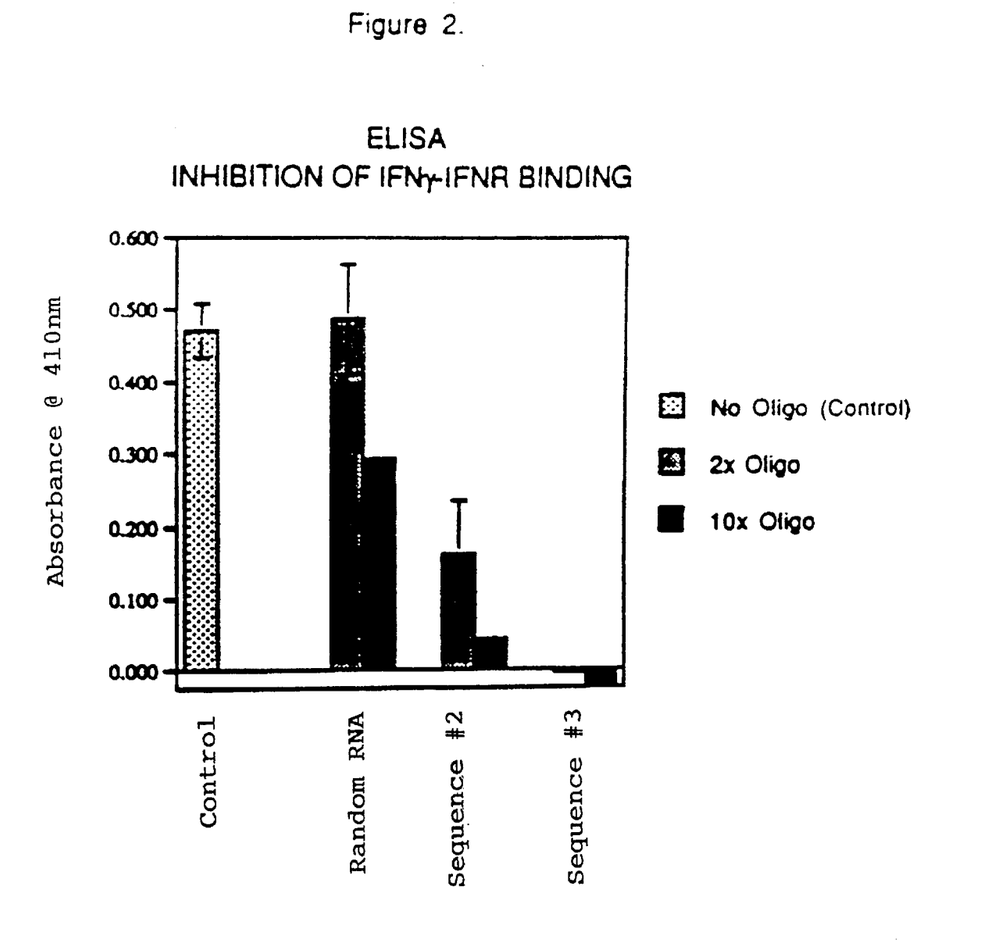

Competition assays were performed to demonstrate that binding of RNA oligonucleotides to IFN-γ blocks the interaction with IFN-γ receptor. In the first competition assay, microtiter wells of a 96-well ELISA plate were coated with 20 pmols of IFN-γ in 50 μl of 150 mM $Na_2CO_3$, 35 mM $NaHCO_3$ pH 9.6 for about 16 hours at 4° C. Various amounts of oligonucleotide (12 or 60 pmols) were added to different wells in 50 μl binding buffer (25 mM Tris-HCl pH 7.5, 150 mM NaCl, 3 mM $MgCl_2$) and incubated for about 5 minutes at room temperature (ca. 23° C.) to allow for binding of the oligonucleotide and the IFN-γ. After incubation, 6 pmols of IFN-γ receptor protein were added in 50 μl binding buffer and the solution was incubated for at least 120 minutes at 37° C. The IFN-γ receptor used for this assay was a recombinant soluble fusion protein consisting of the extracellular domain of the human IFN-γ receptor at the amino end of the protein fused to a mouse kappa light chain immunoglobulin at the carboxyl terminus. After washing with binding buffer, the amount of receptor bound to IFN-γ was determined by adding an enzyme-linked antibody agaist the mouse kappa light chain portion of the fusion protein [1:500 dilution of antibody (Caltag Laboratories) in phosphate-buffered saline containing 1 mg/ml bovine serum albumin] for 60 minutes at 37° C. followed by a chromogenic substrate for the linked enzyme [$H_2O_2$/ABTS (Boehringer Mannheim)], and incubation for an additional 30 minutes at room temperature. The anti-kappa chain antibody does not interfere with the binding of the IFN-γ to its receptor. A reduction in the amount of receptor bound to IFN-γ in the presence of test oligonucleotide indicated that the oligonucleotde blocked the interaction of the cytokine with its receptor. All tested oligonucleotides of the instant invention blocked binding of IFN-γ to its receptor. In contrast a pool of random-sequence oligonucleotides had a minimal effect on the receptor binding. FIG. 2 presents representative results of assays testing the inhibition by oligonucleotides SEQ ID NOS: 2 and 3.

Figure 3:
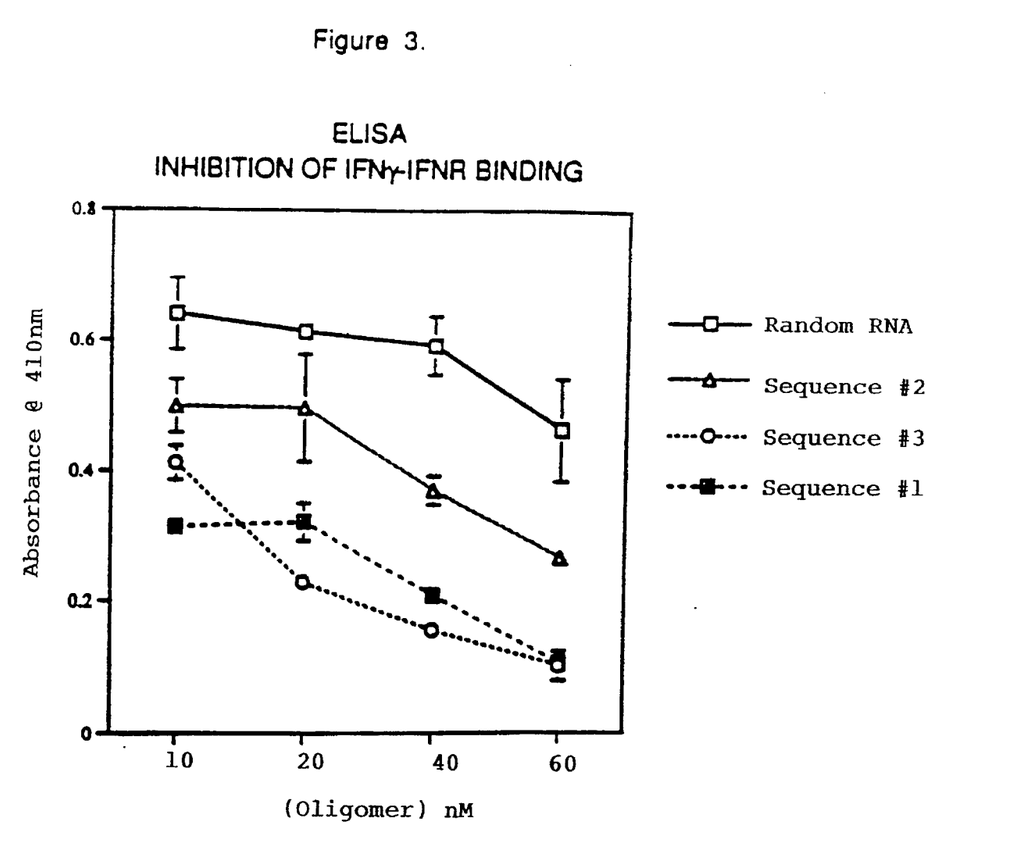

A second competition assay was also performed to demonstrate the ability of oligonucleotides to inhibit IFN-γ binding to its receptor. In this assay, wells of the microtiter plate were coated with 8 pmols of the recombinant IFN-γ receptor fusion protein described above (in 50 μl phosphate-buffered saline for about 16 hours at 4° C.). IFN-γ (2 pmols) was incubated with various amounts of oligonucleotide in 50 μl binding buffer (25 mM Tris-HCl pH 7.5, 150 mM NaCl, 3mM MgCl$_2$) for 5 minutes at room temperature and then the solutions were added to wells containing the receptor protein (final volume 100 µl) to allow binding of receptor and ligand. After washing, the amount of IFN-γ bound to receptor was determined using nonneutralizing anti-IFN-γ antibody (Biosource International) in an enzyme-linked detection assay (Horseradish peroxidase-coupled goat anti-mouse Fc antibody, Accurate Chemical and Scientific Corp.). Reduction of IFN-γ binding in the presence of oligonucleotide indicated inhibition of the receptor-ligand interaction by the oligonucleotides. FIG. 3 presents representative results for the second assay with three oligonucleotides of the instant invention (SEQ ID NOS: 2, 3, and 11) and a mixture of 98 base random sequence RNA for comparison. As is evident from these results, the oligonucleotides of the instant invention are more effective at inhibiting the interaction of IFN-γ and its receptor than the mixture of random-sequence RNA.

---

What is claimed is:

1. An oligonucleotide selected from the group consisting of those having SEQ ID NOS: 1–39.

2. The oligonucleotide of claim 1 that binds with the target IFN-γ at a $K_d$ of not greater than about 30 nM.

* * * * *

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
        ( A ) LENGTH:97 BASES
        ( B ) TYPE:NUCLEIC ACID
        ( C ) STRANDEDNESS: SINGLE
        ( D ) TOPOLOGY:LINEAR     ( i i i ) HYPOTHETICAL: NO     ( x i ) SEQUENCE DESCRIPTION: SEQ ID NO: 1:

```
GGGAGAAGUA  GUGUAGGAAU  UCGAGCAAGA  AGUCCCUGAG  GAGUGAUGUC      50
AUUCCUGCCC  CAUGAUAUGG  AGACUUCUUA  ACUCGAGAGG  UCACAGU         97
```

( 2 ) INFORMATION FOR SEQ ID NO:2:

( i ) SEQUENCE CHARACTERISTICS:
        ( A ) LENGTH:98 BASES
        ( B ) TYPE:NUCLEIC ACID
        ( C ) STRANDEDNESS: SINGLE
        ( D ) TOPOLOGY:LINEAR     ( i i i ) HYPOTHETICAL: NO     ( x i ) SEQUENCE DESCRIPTION: SEQ ID NO: 2:

```
GGGAGAAGUA  GUGUAGGAAU  UCAUUUAAGG  GACCUUCUUG  CACUUGGAUA      50
GCCUUUCUUG  AGGGGCCAGU  UCAUCUCUCC  AGCUCGAGAG  GUCACAGU        98
```

( 2 ) INFORMATION FOR SEQ ID NO:3:

( i ) SEQUENCE CHARACTERISTICS:
        ( A ) LENGTH:98 BASES
        ( B ) TYPE:NUCLEIC ACID
        ( C ) STRANDEDNESS: SINGLE
        ( D ) TOPOLOGY:LINEAR     ( i i i ) HYPOTHETICAL: NO     ( x i ) SEQUENCE DESCRIPTION: SEQ ID NO: 3:

```
GGGAGAAGUA  GUGUAGGAAU  UCUAAGUUGA  GGCUCGUACU  UGUCCUUUGA      50
UUUUCUGUGU  GGGAUGUUAA  UAUUCGUGUG  GUCUCGAGAG  GUCACAGU        98
```

( 2 ) INFORMATION FOR SEQ ID NO:4:

( i ) SEQUENCE CHARACTERISTICS:
        ( A ) LENGTH:97 BASES
        ( B ) TYPE:NUCLEIC ACID
        ( C ) STRANDEDNESS: SINGLE
        ( D ) TOPOLOGY:LINEAR     ( i i i ) HYPOTHETICAL: NO ( x i ) SEQUENCE DESCRIPTION: SEQ ID NO: 4:

GGGAGAAGUA GUGUAGGAAU UCUUGUUCCU AGUCCUAGCG AAAUUGUUGA 50

UUAAAAAGUG GUGCUCGUCC UAACUCGAUA UCUCGAGAGG UCACAGU 97

( 2 ) INFORMATION FOR SEQ ID NO:5:

( i ) SEQUENCE CHARACTERISTICS:
        ( A ) LENGTH:98 BASES
        ( B ) TYPE:NUCLEIC ACID
        ( C ) STRANDEDNESS: SINGLE
        ( D ) TOPOLOGY:LINEAR     ( i i i ) HYPOTHETICAL: NO     ( x i ) SEQUENCE DESCRIPTION: SEQ ID NO: 5:

GGGAGAAGUA GUGUAGGAAU UCACAAGGAC CCCUGCUUUC CCGGACCUCA 50

UUCCCAUAAG UUGUAUGGCG GGAGUUUCUG GACUCGAGAG GUCACAGU 98

( 2 ) INFORMATION FOR SEQ ID NO:6:

( i ) SEQUENCE CHARACTERISTICS:
        ( A ) LENGTH:98 BASES
        ( B ) TYPE:NUCLEIC ACID
        ( C ) STRANDEDNESS: SINGLE
        ( D ) TOPOLOGY:LINEAR     ( i i i ) HYPOTHETICAL: NO     ( x i ) SEQUENCE DESCRIPTION: SEQ ID NO: 6:

GGGAGAAGUA GUGUAGGAAU UCUAUUGCCU CAGAGAGACU CAACGUCACU 50

GGAAUGCCAA UCUAUACAUG UUGGUUUUCG CCCUCGAGAG GUCACAGU 98

( 2 ) INFORMATION FOR SEQ ID NO:7:

( i ) SEQUENCE CHARACTERISTICS:
        ( A ) LENGTH:98 BASES
        ( B ) TYPE:NUCLEIC ACID
        ( C ) STRANDEDNESS: SINGLE
        ( D ) TOPOLOGY:LINEAR     ( i i i ) HYPOTHETICAL: NO     ( x i ) SEQUENCE DESCRIPTION: SEQ ID NO: 7:

GGGAGAAGUA GUGUAGGAAU UCUGUCUCCA GUACCUCUGA UUCUAUAAAA 50

GUCUUACGUA GAAUGCCCUC GAUAAUUUAU AUCUCGAGAG GUCACAGU 98

( 2 ) INFORMATION FOR SEQ ID NO:8:

( i ) SEQUENCE CHARACTERISTICS:
        ( A ) LENGTH:98 BASES
        ( B ) TYPE:NUCLEIC ACID
        ( C ) STRANDEDNESS: SINGLE
        ( D ) TOPOLOGY:LINEAR     ( i i i ) HYPOTHETICAL: NO     ( x i ) SEQUENCE DESCRIPTION: SEQ ID NO: 8:

GGGAGAAGUA GUGUAGGAAU UCUAAGUUGA GGCUCGUAUU UCGCCGGAUC 50

GUCUUAGAGU AUAAGAGACU UGGUCUAUUC ACCUCGAGAG GUCACAGU 98

( 2 ) INFORMATION FOR SEQ ID NO:9:

( i ) SEQUENCE CHARACTERISTICS:
        ( A ) LENGTH:98 BASES ( B ) TYPE:NUCLEIC ACID
( C ) STRANDEDNESS: SINGLE
( D ) TOPOLOGY:LINEAR ( i i i ) HYPOTHETICAL: NO ( x i ) SEQUENCE DESCRIPTION: SEQ ID NO: 9:

GGGAGAAGUA GUGUAGGAAU UCCCGCAGUG AUUAAAUAUG CAUGGCCAAC         50

UACCUAGGUG UGUAUCUCUC UCCCCUACCU CGCUCGAGAG GUCACAGU           98

( 2 ) INFORMATION FOR SEQ ID NO:10:

( i ) SEQUENCE CHARACTERISTICS:
( A ) LENGTH:98 BASES
( B ) TYPE:NUCLEIC ACID
( C ) STRANDEDNESS: SINGLE
( D ) TOPOLOGY:LINEAR ( i i i ) HYPOTHETICAL: NO ( x i ) SEQUENCE DESCRIPTION: SEQ ID NO: 10:

GGGAGAAGUA GUGUAGGAAU UCUUUUAGAC UGUUCCGGUU UUCUAAACCG         50

UGAGGGUAU ACUCUUAACC CUUGGUGUAU GCCUCGAGAG GUCACAGU            98

( 2 ) INFORMATION FOR SEQ ID NO:11:

( i ) SEQUENCE CHARACTERISTICS:
( A ) LENGTH:97 BASES
( B ) TYPE:NUCLEIC ACID
( C ) STRANDEDNESS: SINGLE
( D ) TOPOLOGY:LINEAR ( i i i ) HYPOTHETICAL: NO ( x i ) SEQUENCE DESCRIPTION: SEQ ID NO: 11:

GGGAGAAGUA GUGUAGGAAU UCCUUUUGUG ACCGCUGGGC ACACAACCGU         50

AGCCACCCUC GAAUUAGCGA CUGCCCGUCG UCUCGAGAGG UCACAGU            97

( 2 ) INFORMATION FOR SEQ ID NO:12:

( i ) SEQUENCE CHARACTERISTICS:
( A ) LENGTH:97 BASES
( B ) TYPE:NUCLEIC ACID
( C ) STRANDEDNESS: SINGLE
( D ) TOPOLOGY:LINEAR ( i i i ) HYPOTHETICAL: NO ( x i ) SEQUENCE DESCRIPTION: SEQ ID NO: 12:

GGGAGAAGUA GUGUAGGAAU UCUCGCCGGA CCGCUGGACC UGACAGGGUC         50

ACCCUCGUGC UGCAUAAACC CCCUUUUCUA GCUCGAGAGG UCACAGU            97

( 2 ) INFORMATION FOR SEQ ID NO:13:

( i ) SEQUENCE CHARACTERISTICS:
( A ) LENGTH:98 BASES
( B ) TYPE:NUCLEIC ACID
( C ) STRANDEDNESS: SINGLE
( D ) TOPOLOGY:LINEAR ( i i i ) HYPOTHETICAL: NO ( x i ) SEQUENCE DESCRIPTION: SEQ ID NO: 13:

GGGAGAAGUA GUGUAGGAAU UCUGAUUCUU GAUGGUAGUG UGAGAUAGAA         50

CGCUCCUUAU CACGCCUACU AUGUGUACCU UCCUCGAGAG GUCACAGU           98

(2) INFORMATION FOR SEQ ID NO:14:

(i) SEQUENCE CHARACTERISTICS:
      (A) LENGTH:98 BASES
      (B) TYPE:NUCLEIC ACID
      (C) STRANDEDNESS: SINGLE
      (D) TOPOLOGY:LINEAR (iii) HYPOTHETICAL: NO (xi) SEQUENCE DESCRIPTION: SEQ ID NO: 14:

| GGGAGAAGUA | GUGUAGGAAU | UCACCUACCG | GUGUCUCAGC | CACCCAACUC | 50 |
| UUAAAAAGGG | AAGUGCUGUC | CUCGGCCUUU | AGCUCGAGAG | GUCACAGU   | 98 |

(2) INFORMATION FOR SEQ ID NO:15:

(i) SEQUENCE CHARACTERISTICS:
      (A) LENGTH:97 BASES
      (B) TYPE:NUCLEIC ACID
      (C) STRANDEDNESS: SINGLE
      (D) TOPOLOGY:LINEAR (iii) HYPOTHETICAL: NO (xi) SEQUENCE DESCRIPTION: SEQ ID NO: 15:

| GGGAGAAGUA | GUGUAGGAAU | UCUAAGGUGA | GGCUCGGUCU | CUUCUCGUCA | 50 |
| UGUAUAUAGC | ACAAGUUGCC | GUCGUUUACU | CCUCGAGAGG | UCACAGU    | 97 |

(2) INFORMATION FOR SEQ ID NO:16:

(i) SEQUENCE CHARACTERISTICS:
      (A) LENGTH:98 BASES
      (B) TYPE:NUCLEIC ACID
      (C) STRANDEDNESS: SINGLE
      (D) TOPOLOGY:LINEAR (iii) HYPOTHETICAL: NO (xi) SEQUENCE DESCRIPTION: SEQ ID NO: 16:

| GGGAGAAGUA | GUGUAGGAAU | UCAUUGUGAG | CUCUGGGUAG | UAUUUACUGC | 50 |
| CACCCUCUGU | AGUUGGAUUC | CUGUCGAGUU | UUCUCGAGAG | GUCACAGU   | 98 |

(2) INFORMATION FOR SEQ ID NO:17:

(i) SEQUENCE CHARACTERISTICS:
      (A) LENGTH:97 BASES
      (B) TYPE:NUCLEIC ACID
      (C) STRANDEDNESS: SINGLE
      (D) TOPOLOGY:LINEAR (iii) HYPOTHETICAL: NO (xi) SEQUENCE DESCRIPTION: SEQ ID NO: 17:

| GGGAGAAGUA | GUGUAGGAAU | UCAUAUUAAU | AUCGACCAUC | GUAUUUCACU | 50 |
| UCUCAGUCCG | GAGUCGUACG | CAGCAUAUUG | ACUCGAGAGG | UCACAGU    | 97 |

(2) INFORMATION FOR SEQ ID NO:18:

(i) SEQUENCE CHARACTERISTICS:
      (A) LENGTH:97 BASES
      (B) TYPE:NUCLEIC ACID
      (C) STRANDEDNESS: SINGLE
      (D) TOPOLOGY:LINEAR (iii) HYPOTHETICAL: NO (xi) SEQUENCE DESCRIPTION: SEQ ID NO: 18:

GGGAGAAGUA GUGUAGGAAU UCACGUAAAA GAAUAUGCUG GCGGUGCGGG 50

UACGAAUAUU CAUGUGAGCA GUUGGACUGU ACUCGAGAGG UCACAGU 97

( 2 ) INFORMATION FOR SEQ ID NO:19:

( i ) SEQUENCE CHARACTERISTICS:
        ( A ) LENGTH:98 BASES
        ( B ) TYPE:NUCLEIC ACID
        ( C ) STRANDEDNESS: SINGLE
        ( D ) TOPOLOGY:LINEAR     ( i i i ) HYPOTHETICAL: NO     ( x i ) SEQUENCE DESCRIPTION: SEQ ID NO: 19:

GGGAGAAGUA GUGUAGGAAU UCAUUAUUGG CCUUGAUAUU AUAUAGCUUC 50

GCUACACUUG GGCGCAAGGU AUUGCCGUUC GUCUCGAGAG GUCACAGU 98

( 2 ) INFORMATION FOR SEQ ID NO:20:

( i ) SEQUENCE CHARACTERISTICS:
        ( A ) LENGTH:96 BASES
        ( B ) TYPE:NUCLEIC ACID
        ( C ) STRANDEDNESS: SINGLE
        ( D ) TOPOLOGY:LINEAR     ( i i i ) HYPOTHETICAL: NO     ( x i ) SEQUENCE DESCRIPTION: SEQ ID NO: 20:

GGGAGAAGUA GUGUAGGAAU UCUACGCUAU CUUUAUAAGU UUGGAUUGUC 50

CUAAGCUAAU UUUUAUCAUA GGAGGGCUA CUCGAGAGGU CACAGU 96

( 2 ) INFORMATION FOR SEQ ID NO:21:

( i ) SEQUENCE CHARACTERISTICS:
        ( A ) LENGTH:98 BASES
        ( B ) TYPE:NUCLEIC ACID
        ( C ) STRANDEDNESS: SINGLE
        ( D ) TOPOLOGY:LINEAR     ( i i i ) HYPOTHETICAL: NO     ( x i ) SEQUENCE DESCRIPTION: SEQ ID NO: 21:

GGGAGAAGUA GUGUAGGAAU UCAGUGCUUA CCGGCCCAGU AACCUAUUGA 50

CGAAGCGUUC CGAGGUAAUC CCGCAUGUAA ACCUCGAGAG GUCACAGU 98

( 2 ) INFORMATION FOR SEQ ID NO:22:

( i ) SEQUENCE CHARACTERISTICS:
        ( A ) LENGTH:98 BASES
        ( B ) TYPE:NUCLEIC ACID
        ( C ) STRANDEDNESS: SINGLE
        ( D ) TOPOLOGY:LINEAR     ( i i i ) HYPOTHETICAL: NO     ( x i ) SEQUENCE DESCRIPTION: SEQ ID NO: 22:

GGGAGAAGUA GUGUAGGAAU UCAACACGCC GGGAACUUAC UUUGACGUUG 50

CGAUCCCCA AUUAUAAGAC UAUCUGGAUC ACCUCGAGAG GUCACAGU 98

( 2 ) INFORMATION FOR SEQ ID NO:23:

( i ) SEQUENCE CHARACTERISTICS:
        ( A ) LENGTH:98 BASES
        ( B ) TYPE:NUCLEIC ACID
        ( C ) STRANDEDNESS: SINGLE ( D ) TOPOLOGY:LINEAR ( i i i ) HYPOTHETICAL: NO ( x i ) SEQUENCE DESCRIPTION: SEQ ID NO: 23:

GGGAGAAGUA GUGUAGGAAU UCUAAGUUGA AGCUCACUAC UGCGUACAUU 50

GAGAGAUUGA CAAUUUCAAU GCGAUGGUUU GCCUCGAGAG GUCACAGU 98

( 2 ) INFORMATION FOR SEQ ID NO:24:

( i ) SEQUENCE CHARACTERISTICS:
    ( A ) LENGTH:98 BASES
    ( B ) TYPE:NUCLEIC ACID
    ( C ) STRANDEDNESS: SINGLE
    ( D ) TOPOLOGY:LINEAR   ( i i i ) HYPOTHETICAL: NO   ( x i ) SEQUENCE DESCRIPTION: SEQ ID NO: 24:

GGGAGAAGUA GUGUAGGAAU UCCUCUCGAA UUACCUACAG UUCACCCCUC 50

UAUGUAAGUG AUUCCUCUUC AAACUACUUC CUCUCGAGAG GUCACAGU 98

( 2 ) INFORMATION FOR SEQ ID NO:25:

( i ) SEQUENCE CHARACTERISTICS:
    ( A ) LENGTH:98 BASES
    ( B ) TYPE:NUCLEIC ACID
    ( C ) STRANDEDNESS: SINGLE
    ( D ) TOPOLOGY:LINEAR   ( i i i ) HYPOTHETICAL: NO   ( x i ) SEQUENCE DESCRIPTION: SEQ ID NO: 25:

GGGAGAAGUA GUGUAGGAAU UCUGAUGCUU UGUUAAAAGC ACGAUAAGUU 50

GAGGCUCGAC UGGGACUCUA AUUUACCUC CGCUCGAGAG GUCACAGU 98

( 2 ) INFORMATION FOR SEQ ID NO:26:

( i ) SEQUENCE CHARACTERISTICS:
    ( A ) LENGTH:98 BASES
    ( B ) TYPE:NUCLEIC ACID
    ( C ) STRANDEDNESS: SINGLE
    ( D ) TOPOLOGY:LINEAR   ( i i i ) HYPOTHETICAL: NO   ( x i ) SEQUENCE DESCRIPTION: SEQ ID NO: 26:

GGGAGAAGUA GUGUAGGAAU UCUAAGUUGA CGCUCGCCAA UUCCUCCGU 50

UCUGAGGGUA AAACGCAUAC UCGUGUUAGG CUCUCGAGAG GUCACAGU 98

( 2 ) INFORMATION FOR SEQ ID NO:27:

( i ) SEQUENCE CHARACTERISTICS:
    ( A ) LENGTH:98 BASES
    ( B ) TYPE:NUCLEIC ACID
    ( C ) STRANDEDNESS: SINGLE
    ( D ) TOPOLOGY:LINEAR   ( i i i ) HYPOTHETICAL: NO   ( x i ) SEQUENCE DESCRIPTION: SEQ ID NO: 27:

GGGAGAAGUA GUGUAGGAAU UCCUCACCUU CAAUGCGCUC CAAAACACCU 50

CUGGGUCAUG CAUGGACCAC CCUCGGGAAA UUCUCGAGAG GUCACAGU 98

( 2 ) INFORMATION FOR SEQ ID NO:28:

( i ) SEQUENCE CHARACTERISTICS:
    ( A ) LENGTH:98 BASES
    ( B ) TYPE:NUCLEIC ACID
    ( C ) STRANDEDNESS: SINGLE
    ( D ) TOPOLOGY:LINEAR ( i i i ) HYPOTHETICAL: NO ( x i ) SEQUENCE DESCRIPTION: SEQ ID NO: 28:

| | | | | | |
|---|---|---|---|---|---|
| GGGAGAAGUA | GUGUAGGAAU | UCUAAGUUGA | UGCUGACUAU | GGAUUCCAGG | 50 |
| CUUUCUGCGU | AUCAUCGUCU | AUGUUUCUA | GUCUCGAGAG | GUCACAGU | 98 |

( 2 ) INFORMATION FOR SEQ ID NO:29:

( i ) SEQUENCE CHARACTERISTICS:
    ( A ) LENGTH:97 BASES
    ( B ) TYPE:NUCLEIC ACID
    ( C ) STRANDEDNESS: SINGLE
    ( D ) TOPOLOGY:LINEAR ( i i i ) HYPOTHETICAL: NO ( x i ) SEQUENCE DESCRIPTION: SEQ ID NO: 29:

| | | | | | |
|---|---|---|---|---|---|
| GGGAGAAGUA | GUGUAGGAAU | UCUAGACUGC | UCUGUUCGAA | UUUCCCAGUG | 50 |
| UAAAUCAGGU | CUUAAUUUCG | UGUAACAAGU | ACUCGAGAGG | UCACAGU | 97 |

( 2 ) INFORMATION FOR SEQ ID NO:30:

( i ) SEQUENCE CHARACTERISTICS:
    ( A ) LENGTH:6 BASES
    ( B ) TYPE:NUCLEIC ACID
    ( C ) STRANDEDNESS: SINGLE
    ( D ) TOPOLOGY:LINEAR ( i i i ) HYPOTHETICAL: NO ( x i ) SEQUENCE DESCRIPTION: SEQ ID NO: 30:

AAGUUG      6

( 2 ) INFORMATION FOR SEQ ID NO:31:

( i ) SEQUENCE CHARACTERISTICS:
    ( A ) LENGTH:8 BASES
    ( B ) TYPE:NUCLEIC ACID
    ( C ) STRANDEDNESS: SINGLE
    ( D ) TOPOLOGY:LINEAR ( i i i ) HYPOTHETICAL: NO ( x i ) SEQUENCE DESCRIPTION: SEQ ID NO: 31:

UGANGCUC      8

( 2 ) INFORMATION FOR SEQ ID NO:32:

( i ) SEQUENCE CHARACTERISTICS:
    ( A ) LENGTH:14 BASES
    ( B ) TYPE:NUCLEIC ACID
    ( C ) STRANDEDNESS: SINGLE
    ( D ) TOPOLOGY:LINEAR ( i i i ) HYPOTHETICAL: NO ( x i ) SEQUENCE DESCRIPTION: SEQ ID NO: 32:

UAAGUUGANG CUCG      14

( 2 ) INFORMATION FOR SEQ ID NO:33:

( i ) SEQUENCE CHARACTERISTICS:
    ( A ) LENGTH:7 BASES
    ( B ) TYPE:NUCLEIC ACID
    ( C ) STRANDEDNESS: SINGLE
    ( D ) TOPOLOGY:LINEAR ( i i i ) HYPOTHETICAL: NO ( x i ) SEQUENCE DESCRIPTION: SEQ ID NO: 33:

GCACCNC       7

( 2 ) INFORMATION FOR SEQ ID NO:34:

( i ) SEQUENCE CHARACTERISTICS:
        ( A ) LENGTH:10 BASES
        ( B ) TYPE:NUCLEIC ACID
        ( C ) STRANDEDNESS: SINGLE
        ( D ) TOPOLOGY:LINEAR     ( i i i ) HYPOTHETICAL: NO     ( x i ) SEQUENCE DESCRIPTION: SEQ ID NO: 34:

GCCACCCUCG       10

( 2 ) INFORMATION FOR SEQ ID NO:35:

( i ) SEQUENCE CHARACTERISTICS:
        ( A ) LENGTH:93 BASES
        ( B ) TYPE:NUCLEIC ACID
        ( C ) STRANDEDNESS: SINGLE
        ( D ) TOPOLOGY:LINEAR     ( i i i ) HYPOTHETICAL: NO     ( x i ) SEQUENCE DESCRIPTION: SEQ ID NO: 35:

AAGUAGUGUA GGAAUUCUAA GUUGAGGCUC GUACUUGUCC UUUGAUUUUC    50

UGUGUGGGAU GUUAAUAUUC GUGUGGUCUC GAGAGGUCAC AGU    93

( 2 ) INFORMATION FOR SEQ ID NO:36:

( i ) SEQUENCE CHARACTERISTICS:
        ( A ) LENGTH:43 BASES
        ( B ) TYPE:NUCLEIC ACID
        ( C ) STRANDEDNESS: SINGLE
        ( D ) TOPOLOGY:LINEAR     ( i i i ) HYPOTHETICAL: NO     ( x i ) SEQUENCE DESCRIPTION: SEQ ID NO: 36:

AAGUAGUGUA GGAAUUCUAA GUUGAGGCUC GUACUUGUCC UUU    43

( 2 ) INFORMATION FOR SEQ ID NO:37:

( i ) SEQUENCE CHARACTERISTICS:
        ( A ) LENGTH:60 BASES
        ( B ) TYPE:NUCLEIC ACID
        ( C ) STRANDEDNESS: SINGLE
        ( D ) TOPOLOGY:LINEAR     ( i i i ) HYPOTHETICAL: NO     ( x i ) SEQUENCE DESCRIPTION: SEQ ID NO: 37:

GGGAGAAGUA GUGUAGGAAU UCUAAGUUGA GGCUCGUACU UGUCCUUUGA    50

UUUUCUGUGU    60

( 2 ) INFORMATION FOR SEQ ID NO:38:

( i ) SEQUENCE CHARACTERISTICS:

-continued (A) LENGTH:48 BASES
(B) TYPE:NUCLEIC ACID
(C) STRANDEDNESS: SINGLE
(D) TOPOLOGY:LINEAR (iii) HYPOTHETICAL: NO (xi) SEQUENCE DESCRIPTION: SEQ ID NO: 38:

GGGAGAAGUA GUGUAGGAAU UCUAAGUUGA GGCUCGUACU UGUCCUUU  48

(2) INFORMATION FOR SEQ ID NO:39:

(i) SEQUENCE CHARACTERISTICS:
(A) LENGTH:40 BASES
(B) TYPE:NUCLEIC ACID
(C) STRANDEDNESS: SINGLE
(D) TOPOLOGY:LINEAR (iii) HYPOTHETICAL: NO (xi) SEQUENCE DESCRIPTION: SEQ ID NO: 39:

GGGAGAAGUA GUGUAGGAAU UCUAAGUUGA GGCUCGUACU  40